(12) United States Patent
Dugand et al.

(10) Patent No.: US 10,688,254 B2
(45) Date of Patent: *Jun. 23, 2020

(54) SAFETY DEVICE FOR A PRE-FILLED INJECTION SYRINGE

(71) Applicant: Nemera La Verpillière S.A.S., La Verpilliere (FR)

(72) Inventors: Pascal Dugand, Estrablin (FR); Sylvain Lanzi, Chirens (FR)

(73) Assignee: Nemera La Verpillière (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/109,409

(22) Filed: Aug. 22, 2018

(65) Prior Publication Data

US 2018/0361079 A1 Dec. 20, 2018

Related U.S. Application Data

(63) Continuation of application No. 13/662,179, filed on Oct. 26, 2012, which is a continuation of application No. PCT/FR2011/050975, filed on Apr. 28, 2011.

(30) Foreign Application Priority Data

Apr. 28, 2010 (FR) ..................................... 10 53280

(51) Int. Cl.
*A61M 5/32* (2006.01)
*A61M 5/31* (2006.01)

(52) U.S. Cl.
CPC ........ *A61M 5/3245* (2013.01); *A61M 5/3243* (2013.01); *A61M 5/3137* (2013.01);
(Continued)

(58) Field of Classification Search
CPC .. A61M 5/3137; A61M 5/321; A61M 5/3243; A61M 5/3245; A61M 5/3257; A61M 5/326; A61M 2005/3139; A61M 2005/3142; A61M 2005/3247; A61M 2005/3261; A61M 2005/3264
See application file for complete search history.

(56) References Cited

U.S. PATENT DOCUMENTS 3,384,082 A 5/1968 Harrold
4,968,305 A 11/1990 Takahashi et al.
(Continued)

FOREIGN PATENT DOCUMENTS

DE 19613035 A1 9/1997
FR 2842112 A1 1/2004
(Continued)

*Primary Examiner* — Shefali D Patel
(74) *Attorney, Agent, or Firm* — St. Onge Steward Johnston & Reens, LLC (57) ABSTRACT

A safety device for an injection syringe including a syringe support, a protective sheath for protecting an injection needle carried by the syringe, the sheath being mounted to slide relative to the syringe support between an injection position in which the needle is uncovered, and a protection position in which the needle is covered, the sheath having an initial grip surface enabling the device to be gripped by a user, and a return spring for urging the sheath into the protection position. The sheath also includes an extender member for extending the initial grip surface and fitted on the sheath in such a manner as to present a larger grip surface, referred to as an enlarged grip surface.

20 Claims, 4 Drawing Sheets

(52) U.S. Cl.
CPC ........... *A61M 5/3202* (2013.01); *A61M 5/326* (2013.01); *A61M 2005/312* (2013.01); *A61M 2005/3139* (2013.01); *A61M 2005/3247* (2013.01); *A61M 2005/3261* (2013.01); *A61M 2005/3264* (2013.01); *Y10T 29/49826* (2015.01)

(56) References Cited

U.S. PATENT DOCUMENTS

| | | | |
|---|---|---|---|
| 5,509,903 | A | 4/1996 | Grendahl et al. |
| 6,319,233 | B1 | 11/2001 | Jansen et al. |
| 6,344,032 | B1 | 2/2002 | Perez et al. |
| 7,374,555 | B2 | 5/2008 | Heinz et al. |
| 8,920,385 | B2 | 12/2014 | Dowds |
| 2004/0167476 | A1 | 8/2004 | Westbye |
| 2006/0036216 | A1 | 2/2006 | Rimlinger et al. |
| 2009/0036839 | A1 | 2/2009 | Phalen |
| 2009/0105663 | A1 | 4/2009 | Brand et al. |
| 2011/0276026 | A1 | 11/2011 | Dowds |

FOREIGN PATENT DOCUMENTS

| | | |
|---|---|---|
| FR | 2922112 A1 | 4/2009 |
| WO | 03077977 A2 | 9/2003 |

SAFETY DEVICE FOR A PRE-FILLED INJECTION SYRINGE

FIELD OF INVENTION

The present invention relates to the field of injecting substances such as medication. It relates more particularly to the field of safety devices for pre-filled injection syringes.

BACKGROUND OF THE INVENTION

A safety device for an injection syringe is already known that has a protective sheath that is triggered at the end of injection so as to cover the injection needle and thus avoid any contamination. An example of such a device is described in document FR 2 922 112.

Generally, such a device has flanges, or a collar, serving as a bearing surface for the fingers of the user performing the injection.

A difficulty lies in the fact that those grip flanges can be too small for people suffering from inflammatory joint pain or who have difficulty in manipulating or in applying sufficient force on items of small size, for example people suffering from rheumatoid arthritis.

SUMMARY OF THE INVENTION

A particular object of the present invention is to provide a safety device that is easier to manipulate, in particular for users who encounter difficulties in gripping the device.

To this end, the invention provides a safety device for an injection syringe, the safety device comprising:
  a syringe support;
  a protective sheath for protecting an injection needle carried by the syringe, the sheath being mounted to slide relative to the syringe support between an injection position in which the needle is uncovered, and a protection position in which the needle is covered, the sheath having a grip surface enabling the device to be gripped by a user and referred to as the "initial" grip surface; and
  a return spring for urging the sheath into the protection position; the sheath further includes an extender member for extending the initial grip surface and fitted on the sheath in such a manner as to present a larger grip surface, referred to as an "enlarged" grip surface.

Thus, it is proposed to add an element to the sheath suitable for making the device easier to grip. In such circumstances, it may be advantageous to fit an additional element on the sheath in order to enlarge an initial grip surface rather than to make a large grip surface directly on the sheath. Since it is observed that only some users need a large surface, it is proposed herein to use a device that is standard, for use by users of all types, with the possibility of adapting the safety device to certain users, by adding the extender member to the device. As a result, manufacture is simplified, since a syringe support and a sheath are used that are identical to those used in the past, and thus the same mold can be used, while also providing a guarantee that people who have difficulty in manipulation can use the device without difficulty, because of the possibility of fitting the extender member on the sheath. In addition, it becomes possible to conserve a grip surface area that is relatively small for most users, i.e. to conserve the initial surface provided on the sheath, thereby making it possible to reduce the general size of the safety device and thus to save space for storage and transport of the devices.

It should be observed that the injection syringe is preferably pre-filled and is generally a glass syringe, of standard shape and size, e.g. a 0.5 milliliter (mL) or a 1 mL syringe. The syringe is of tubular shape, presenting an injection needle at its distal end, possibly mounted on a fastener endpiece often referred to as a "luer" lock, and presenting a collar at its proximal end, which collar is made integrally with the body of the syringe. The collar of the syringe serves in particular to fasten the syringe on the syringe support, e.g. by snap-fastening. It should also be observed that the syringe support is generally made of plastics material, thus providing the advantage of making the functional portions more easily by making them on the support rather than on the syringe, which is made of glass. For example, the syringe support may carry lugs for snap-fastening with the collar of the syringe, guide elements for guiding the sheath to its protection position, locking elements for locking the device in the protection position, and/or retractable elements for preventing the device from moving while in the injection position. It should also be observed that the sheath is generally a part made of plastics material and that performs several functions. The sheath may include one or more of the following elements: retractable means for compressing the spring to hold the device in the injection position; guide means for guiding the sheath while it is moving to the protection position; means for preventing the sheath from moving while in the protection position; and a tubular portion for covering the needle and for preventing a user's finger from touching the needle once the device is in the protection position.

The enlarged grip surface is preferably a surface that covers the initial grip surface and that extends in a plane substantially perpendicular to the axis of the device.

By means of the above-described extender member, the inventors propose taking an additional step towards standardizing manufacturing methods; not only is it possible to use a standard glass syringe, but it is also possible to a use a standard sheath that can be used by users of all types, possibly after an extender member has been added.

The safety device of the invention may also include one or more of the following characteristics, taken singly or in combination.

The extender member includes an annular skirt projecting from the enlarged grip surface. This annular skirt is preferably located on the distal side relative to the enlarged grip surface. It is coaxial about the sheath, being placed around the sheath, and it may perform a function of centering the extender member on the sheath, by holding the enlarged grip surface in position on the axis of the sheath and thus preventing it from moving away from the axis as a result of the user moving in asymmetrical manner on one side of the grip surface. The annular skirt may also act as a support for a label that provides information about the medication to be found in the syringe. The advantage of the tubular skirt is that it does not present any portions in relief, unlike a sheath, which may for example carry clips for preventing the sheath from moving when in the protection position, thus making it relatively unsuitable for receiving a label. The annular skirt makes it possible to present a surface area free of portions in relief that is relatively large, and ideal for carrying a label.

The spring is in a compressed configuration when the sheath is in the injection position, and the annular skirt is a skirt for masking the spring in the compressed configuration. Often, the sheath and the syringe support are made of a material that is transparent or translucent, so as to enable the user to see the contents of the syringe that is located inside the device. As a result, the user generally also sees the spring of the safety device. However, the spring is usually a part that is made of metal and can thus give users negative preconceptions about the sterility of the injected substance or the cleanliness of the system. Although the spring never comes into contact with the injected substance, it gives a general impression of being a device that is technical and "not hygienic". By hiding it by means of an opaque annular skirt, the user is given the impression that the safety device is more sterile or cleaner.

The sheath includes means for preventing the sheath from moving in the protection position, preferably snap-fastener means, and the annular skirt covers these means for preventing the sheath from moving. The annular skirt thus makes it possible firstly to mask the means for preventing the sheath from moving, thus improving its appearance, and secondly makes these means more difficult for the user to access, thereby preventing the safety device from being re-used once it has taken up its protection position. This advantage is particularly advantageous for preventing used devices being re-used and/or for reducing any risk of injury. Furthermore, the skirt thus presents an even larger surface area suitable for carrying a label.

The annular skirt extends in the longitudinal direction to the distal end of the device, so as to cover all of the needle of the syringe when the sheath is in the protection position. In addition to the fact that the annular skirt is capable of presenting a very large surface area for carrying a label, this can enable the extender member to perform the function of covering the needle in the injection position and thereby simplify the remainder of the sheath by making this function easier to perform, which may be particularly advantageous for enabling the remainder of the sheath to be unmolded. The portion of the sheath that covers the needle in the protection position often needs to present a reduction in diameter in order to prevent a finger being inserted after the safety position has been taken up. This reduction in diameter makes the sheath difficult to unmold. By making an extender member that covers the entire needle, it is possible to reduce the length of the initial sheath and thus to avoid the need of providing this reduction in diameter, thereby making it easier to unmold.

The annular skirt comprises a main tubular portion and a distal end of diameter that decreases relative to that of the main tubular portion. In other words, the distal end of the tubular portion is of tapering shape.

The enlarged grip surface presents two opposite radial ends, these ends being curved towards the distal end of the device. The curved ends make gripping the device easier for users who have difficulties, in particular because it prevents the device from escaping from the hand.

The enlarged grip surface presents anti-skid portions in relief, e.g. ribs.

The enlarged grip surface is made out of a material that is softer than the remainder of the safety device, or is covered completely or in part with such a material. This softer material provides more comfort when gripping the safety device, in particular for users having skin that might be sensitive to sharp edges.

The device includes snap-fastener means for snap-fastening the extender member to the sheath and carried by the extender member and/or by the sheath. These means are carried in particular by the initial grip wall of the device.

The enlarged grip surface presents two opposite radial ends that are connected together by two sides, each presenting a flat. These flats enable the device to be oriented during the method of manufacturing the device, and they also make it easier to store, preventing the device from rolling.

The sheath and the support are made of a material that is translucent or transparent, and the extender member is made of a material that is opaque. The extender member thus serves to hide certain elements. In addition, it may serve as means for indicating the type of medication that is to be found in the syringe. For example, it may be of a color that indicates the kind of medication that is in the syringe, or indeed the syringe capacity, or the filling percentage of the syringe.

The extender member is put into place via the distal end of the device. Thus, there is no danger of the user separating the extender member from the sheath when injecting the substance, i.e. when pressing on the extender member while directing a force towards the proximal end of the device.

The device includes a tamperproofing sleeve fastened to the device by a breakable connection, preferably integrally molded with the extender member. This makes it possible to ensure that the device has not been opened prior to injection.

The invention also provides a set of two devices as described above, each presenting a syringe support and a sheath that are identical in both devices and respective extender members for extending the grip surface that are different from one device to the other. For example, the extender members may be of different shapes, colors, and/or materials, thus making it possible to distinguish between different types of safety device, of syringe, or of medication. Possibly, one of the devices has an extender member while the other device does not have one at all.

The invention also provides an assembly of a device as described above together with a pre-filled syringe. The syringe is preferably made of glass and has a collar integrally formed with the syringe body. The collar of the syringe is an element distinct from the initial grip surface and from the enlarged grip surface.

The invention also provides a method of assembling a device as described above, in which method a portion of the sheath is initially assembled with the support, after which the extender member is fitted to said portion of the sheath, preferably via the distal end of the sheath.

This assembly method is preferably followed by a step of assembling a pre-filled syringe in the safety device.

BRIEF DESCRIPTION OF THE DRAWINGS

The invention can be better understood on reading the following description given purely by way of example and made with reference to the drawings, in which.

DETAILED DESCRIPTION OF THE INVENTION

FIGS. 1a, 1b, 2a, and 2b show an assembly 10 of a safety device 11 and an injection syringe 12. The safety device 11 comprises a syringe support 14, a protective sheath 16, and return means 18. The sheath 16 is mounted to slide relative to the support 14 between an injection position and a protection position, under drive from the return means 18, constituted in this example by a spring in compression.

Figure 1A:
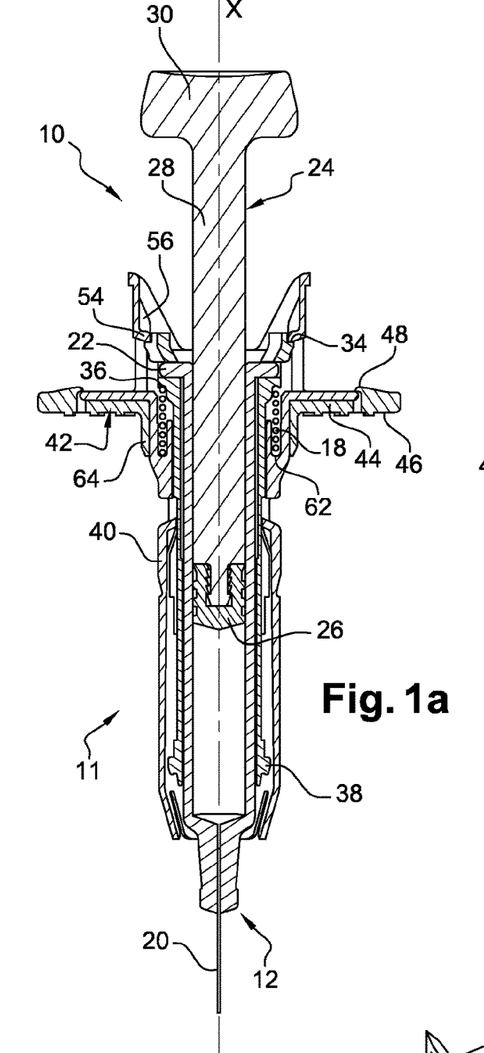
FIGS. 1a and 1b are longitudinal section views of the assembly comprising a safety device and a syringe in a first embodiment, shown respectively in the injection position and in the protection position.
Figure 1B:
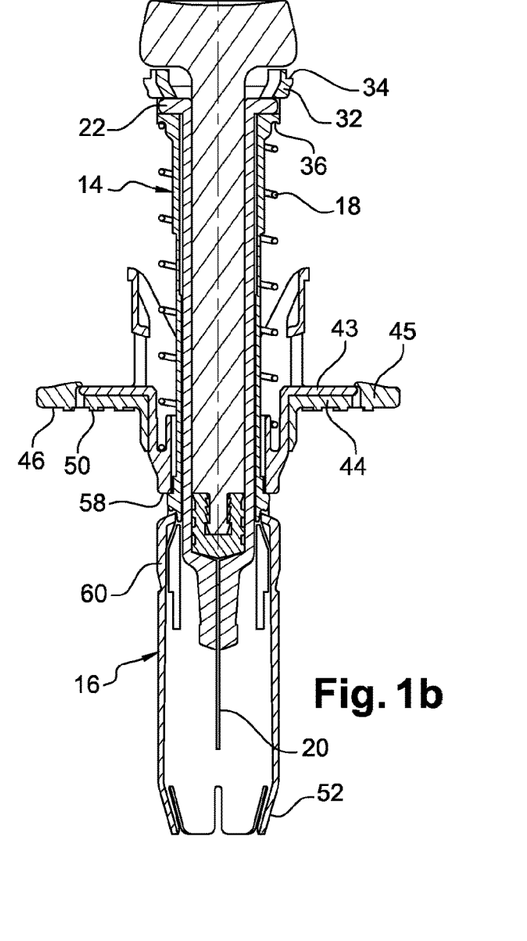

The syringe 12 is a glass syringe, pre-filled with a substance. The syringe 12 is a standard glass syringe, e.g. a 0.5 mL or a 1 mL syringe. It comprises a glass body defining a container for the substance and carrying at its distal end an injection needle 20, possibly connected via a luer lock. When the device 11 is in the injection position, the needle 20 is uncovered, i.e. it is visible to the user, and when the device 11 is in the protection position, the needle 20 is covered by the sheath 16, so as to prevent accidental pricking after injection. The glass syringe body also includes a collar 22 at its proximal end, which collar is made integrally with the syringe body. The collar 22 serves in particular to fasten the body of the syringe 12 on the support 14. The syringe 12 also includes a piston 24 having an elastomer base 26, a rod 28, and a plunger 30. The piston 24 is mounted to slide in the syringe body so as to be capable of injecting the substance contained in the syringe body.

The syringe support 14 is a plastics material part that is generally tubular in shape. At its proximal end, it carries snap-fastener means 32 for permanently engaging the collar 22 of the syringe on the support 14. In this example, the means 22 comprise lugs distributed angularly around the longitudinal axis X of the device so as to form an abutment in the direction X and prevent the collar 22 from moving between the lugs and a circular seat made on the support 14. The support 14 extends from the proximal end of the syringe body 12 to the vicinity of its distal end. More precisely, the support 14 allows the distal end of the syringe body 12 to project a little, as can be seen in FIG. 1a. The support 14 also includes an abutment 34 for retaining the syringe support in the injection position, and an abutment 36 forming a seat for the spring 18. The abutments 34 and 36 are arranged on the proximal end of the support 14. The support 14 also includes means 38 for preventing the support from moving relative to the sheath 16 when in the protection position, which means are arranged on the distal end of the support 14. More precisely, the means 38 compromise lugs that become inserted in slots in the sheath 16 once the device is in the protection position, under drive from the spring, so as to prevent the support 14 from moving relative to the sheath 16. The support 14 also includes fluting in a portion of its tubular outside surface, which fluting extends in the longitudinal direction X and serves to guide the sliding of the support 14 relative to the sheath 16 while these two parts are being assembled together, and while the sheath is moving into the protection position.

Figure 2A:
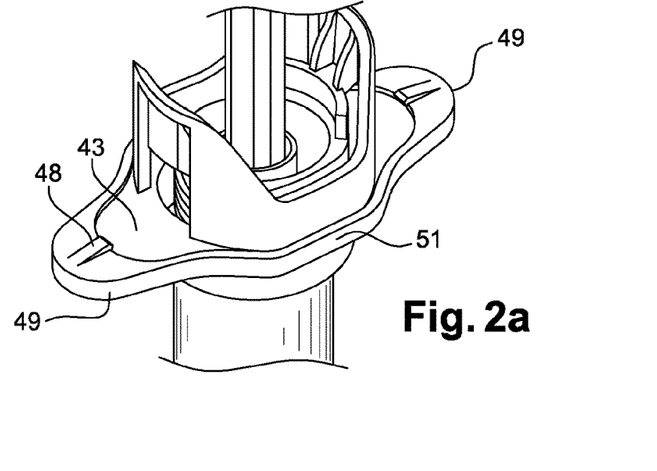
FIGS. 2a and 2b are perspective views, respectively from above and from below of a portion of the FIG. 1a assembly.

The protection sheath 16 is a plastics material part of generally tubular shape. In this invention, it comprises two parts that are fitted together. More precisely, the sheath 16 comprises a part 40 that is referred to below as the "initial" sheath 40, and an extender member 42 for extending the initial extension surface. The initial sheath 40 is a sheath that, in this example, is capable of being used on its own as the sheath of the device 11, the member 42 not being essential for its operation. In particular, the initial sheath 40 has a grip wall 43 carrying a grip surface 44 enabling a user to grip the device 11, and referred to as the "initial" grip surface. This initial surface 44 is a surface located at the distal end of the wall 43, it extends in a radial plane substantially perpendicular to the longitudinal axis X, and it includes at least two diametrically opposite portions in the form of grip flanges. The initial surface 44 may also be in the form of a circular collar extending around the initial sheath 40 and lying in a radial plane. The initial surface 44 is configured in such a manner that in order to inject the substance contained in the syringe 12, the user engages two fingers, generally the index and middle fingers, under the surface 44 on either side of the axis X, and places the thumb on the plunger 30 in order to move the piston 24. The member 42 enables the device 11 to be adapted to some particular utilization in which it is necessary to have a grip surface that is larger than usual. To this end, the member 42 has a wall 45 presenting a surface 46 on its distal side that is referred to as the "enlarged" grip surface and that is fitted on the initial surface 44 in such a manner that the device 11 presents a grip surface that is larger than the initial surface 44. In this example, the enlarged surface 46 completely covers and enlarges the initial surface 44. As can be seen in FIGS. 1a and 1b, the surface 46 presents a length in the radial direction that is greater than the corresponding length of the initial surface 44. The member 42 is fastened on the initial sheath 40 by snap-fastener means 48, comprising in this example lugs 48 that extend from the top (or proximal surface) of the wall 45 carrying the enlarged grip surface 46. The means 48 enable the member 42 to be snap-fastened on the initial sheath 40, and more precisely on the initial grip wall 43. It should be observed that the enlarged grip surface 46 presents anti-skid portions in relief 50. Furthermore, as can be seen in FIG. 2a, the enlarged grip surface 46 presents two opposite radial ends 49 that are connected together by two sides 51, each presenting a respective flat and making it easier to orient the device 11 during assembly, transport, and storage.

The protective sheath 16 also includes certain functional portions, which are carried by the initial sheath 40 in this example.

More precisely, the sheath has a distal end 52 arranged to prevent a person's finger coming into contact with the needle when the sheath 16 is in the protection position. For this purpose, the end 52 presents a reduction in diameter to prevent a finger being inserted inside the sheath 16. In this example, the end 52 is split so as to present "petals" that enable the initial sheath 40 to be unmolded as a result of the elasticity of the petals. The sheath 16 also includes retaining means 54 for retaining the device in the injection position, the means 54 being retractable when the piston reaches the end of its stroke, thereby triggering the movement into the protection position. More precisely, the means 54 comprise lugs at the proximal end of the device 11 and extending radially inwards so as to retain the abutments 34. The sheath 16 preferably has two diametrically opposite lugs 54, each carried by a resilient tab presenting a ramp 56 co-operating with the piston 24 so that the lugs 54 are spaced apart outwards and thus no longer retain the abutments 34 when the piston reaches the end of its stroke.

Furthermore, the sheath 16 presents means 58 for preventing the sheath from moving when in the safety position, which means 58 co-operate with the means 38 provided on the support 14. In this example, the means 58 comprise two diametrically opposite slots defined in particular by two resilient tabs 60 capable of moving radially so that the lugs 38 can be forced past them under drive from the spring so as to snap into the slots 58.

The sheath 16 also has an abutment surface 62 forming a seat for the distal end of the spring 18. The surface 62 is defined by the end of a groove for receiving the spring 18, serving to center the spring while the device 11 is being assembled. It should be observed that the inside wall of the groove 62 is not annular, but comprises two diametrically opposite portions spaced apart by a gap making it possible for the guide fluting of the support 14 to slide relative to the sheath 16.

In this example, the extender member 42 comprises an annular skirt 64 projecting from the enlarged grip surface 46, and thus located on the distal side of the member 42. The skirt 64 serves to center the extender member 42 on the initial sheath 40. In addition, the annular skirt 64 is a skirt for masking the spring 18 in the compressed configuration. The initial sheath 40 and the support 14 are preferably made of a transparent material, while the member 42 is made of an opaque material, so that the skirt 64 serves to hide the spring while it is compressed.

The operation of the assembly 10 shown in FIGS. 1a, 1b, 2a, and 2b is described below.

When the user seeks to perform an injection, the device is in the injection position, i.e. the sheath 16 does not cover the needle, as shown in FIG. 1a. In principle, the needle should be covered by a cap that the user removes in order to begin the injection. The needle 20 is then inserted into the user's body or into the body of a patient and injection is begun by the thumb pressing down on the piston 24 while two fingers are engaged under the enlarged grip surface 46. Once the substance has been fully injected into the patient's body, the piston reaches the end of its stroke, and the bottom end of the plunger 30 co-operates with the ramps 56 so as to move the lugs 54 apart and release the spring 18 so that it can relax. As it decompresses, the spring 18 pushes against the surface 36 of the syringe support 14 so that the support 14 and thus the syringe 12 slide relative to the sheath 16 moving "upwards" relative to the sheath 16 in order to reach a protection position, as shown in FIG. 1b. In this protection position, the needle 20 is completely covered by the sheath 16 and it is not possible to make contact with the needle since it is not possible to pass a finger through the end 52. Furthermore, the device 11 is locked in this protection position by the means 38 and 58 that prevent the sheath 16 from sliding relative to the support 14.

One example of assembling the device 11 comprises the following steps. The device 11 is initially put together and pre-assembled without the syringe 12, such that the syringe can be manufactured independently of the device 11. This is particularly advantageous: the laboratory that manufactures the medication for injection can thus fill the syringe 12 and can itself fit it in the pre-assembled device 11, merely by inserting the syringe and without any need to use a relatively complex machine for assembling the device 11. That assembly is performed directly by the manufacturer of the device 11 in a different factory. The manufacturer of the device 11 begins by injection molding the elements 40, 42, and 14. Thereafter, the spring 18 is fitted inside the initial sheath 40 via the proximal end of the sheath 40 by being inserted into the groove 62, and then the support 14 is inserted inside the sheath 40 and the spring 18. By pressing on the support 14, the spring 18 is compressed until the abutments 34 of the support 14 snap-fasten with the lugs 54 of the sheath 40. This produces a device having a pre-compressed spring, and having a relatively small grip surface 44 that is directly usable as such. In order to enable the device 11 to be used with greater comfort, it is possible to fit the extender member 42 for extending the grip surface. Under such circumstances, the member 42 is inserted via the distal end of the initial sheath 40 and the means 48 snap-fasten on the initial grip wall 43. This provides a fully assembled device 11 including the pre-compressed spring 18, suitable for the device 11 to be transported to a laboratory where the pre-filled syringe 12 can be assembled in the device 11 merely by inserting the syringe through the proximal end of the device 11 so as to cause the collar 22 of the syringe to snap-fasten in the elements 32, and without any need to provide an assembly machine suitable for compressing the spring.

Other embodiments of the member 42, similar to the embodiment described above, are shown in the figures.

Figures 2B, 3, 4, 5:
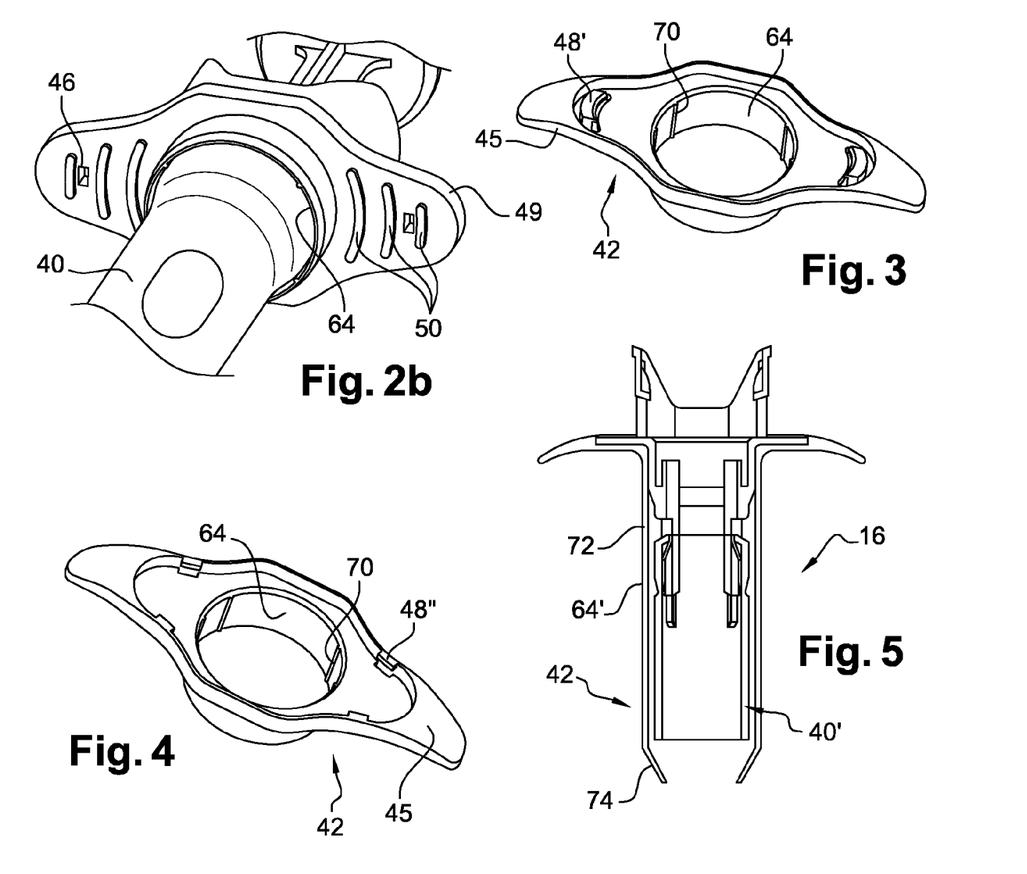
FIG. 3 is a perspective view of an extender member for a safety device in a second embodiment.
FIG. 4 is a perspective view of an extender member for a safety device in a third embodiment.
FIG. 5 is a longitudinal section view of a sheath of a safety device in a fourth embodiment.

In FIG. 3, the snap-fastener means 48' do not project from the enlarged grip wall 45 but are housed inside a recess formed in said wall 45, so as to avoid projecting beyond the proximal surface of the wall 45, for reasons of improved appearance. Furthermore, in FIG. 3, there can be seen the inside orifice of the annular skirt 64 with projecting elements 70 for positioning the member 42 around the initial sheath 40. In FIG. 4, the snap-fastener means 48" are slightly different from the means 48 in FIG. 1a. They comprise lugs extending radially from the proximal surface of the wall 45, without projecting beyond said wall in the longitudinal direction X, thereby making them more discreet than the lugs 48.

In FIG. 5, the annular skirt 64' extends in the longitudinal direction over a greater distance than the skirt 64. It may thus serve as a larger support for a label. In addition, and in particularly advantageous manner, the skirt 64' covers the means 38 and 58 for preventing the sheath 16 from moving relative to the support 14, thereby serving to mask them and to make them inaccessible, and thus serving to prevent the device 11 from being reactivated. The annular skirt 64' extends in the longitudinal direction X to the distal end of the device 11 so as to cover all of the needle 20 of the syringe when the sheath 16 is in the protection position. More precisely, the annular skirt 64' comprises a main tubular portion 72 and a distal end 74 of diameter that decreases relative to the diameter of the main tubular portion 72 in order to prevent a finger being inserted. In this embodiment, the initial sheath 40' does not have the end 52 of the initial sheath 40 of FIG. 1b, with the diameter-reduction function being provided by the skirt 64'.

Figure 9:
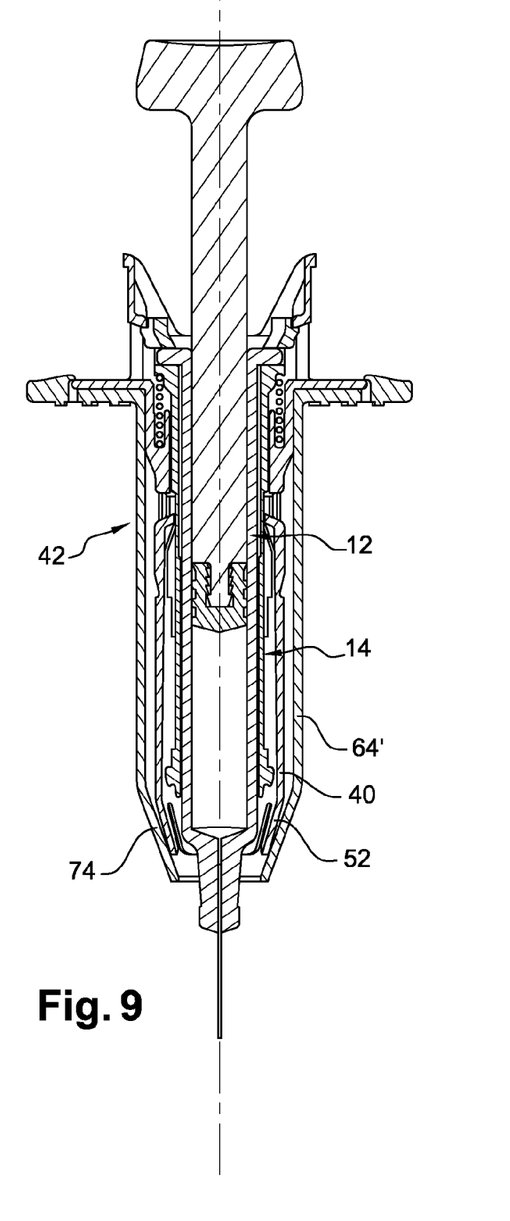
FIG. 9 is a view similar to FIG. 1a of an assembly in an eighth embodiment.

In FIG. 9, the annular skirt 64' is substantially the same as in FIG. 5, and the initial sheath 40 is substantially the same as in FIG. 1b. In particular, the initial sheath 40 has the tapering end 52 for preventing insertion of a finger. This end 52 is covered by the tapering end 74 of the skirt 64', thereby providing even better protection of the needle once used.

Figure 10:
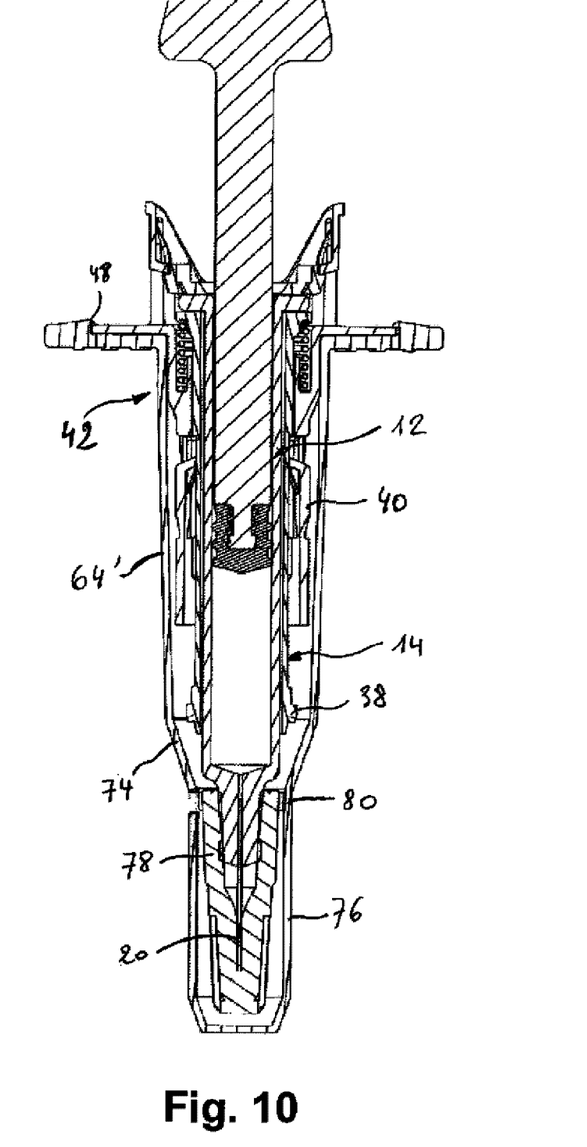
FIG. 10 is a view similar to FIG. 1a of an assembly in a ninth embodiment.

In FIG. 10, the device is substantially the same as in FIG. 9. The tapering end 74 of the annular skirt 64' is extended by a closed sleeve 76 that covers the needle 20 and that is referred to as the "tamperproofing" sleeve, which sleeve is fastened to the device by means of a breakable connection so as to enable the user to verify that the device has not been opened prior to injection. More precisely, the extender member 42 is molded integrally with the tamperproofing sleeve 76, the sleeve 76 being connected to the annular skirt 64' by breakable bridges 80 that are distributed around the circumference of the sleeve 76, between the sleeve 76 and the tapering end 74 of the annular skirt 64'. The needle 20 is also protected by a removable cap 78. In addition, the fastener lugs 48 of the member 42 on the initial sheath 40 provide tamperproof fastening of the member, i.e. once the member 42 has been separated from the sheath 40 they do not allow the member 42 to be fastened once more on the sheath 40: separation of the member 42 is not reversible.

Prior to utilization, it is thus very easy to verify that the device has not been opened. In order to perform an injection, the user breaks the bridges 80 to separate the sleeve 76 from the skirt 64' and takes away the cap 78 so as to lay bare the needle 20. Once the bridges 80 have been broken, it is not possible to fasten the sleeve 76 once more on the annular skirt 64'.

Figure 8:
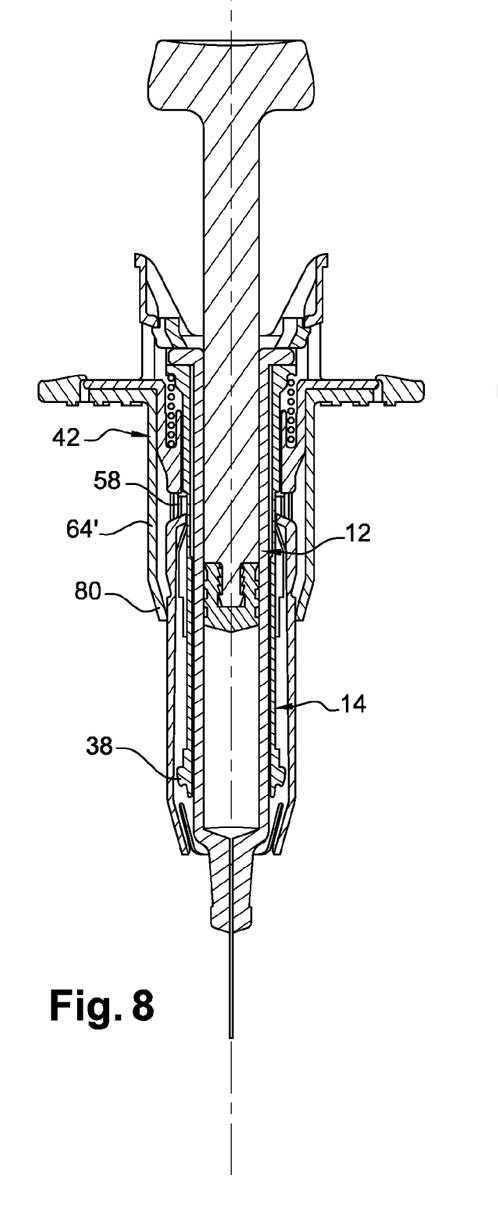
FIG. 8 is a view similar to FIG. 1a of an assembly in a seventh embodiment.

In FIG. 8, the annular skirt 64' does not extend to the distal end of the safety device, unlike in FIGS. 5 and 9. Nevertheless, it extends over a relatively long distance around the initial sheath 40, a distance that is sufficient to cover the means 38 and 58 for preventing the sheath 16 from moving relative to the support 14, so as to mask those means and make them inaccessible. In addition, the surface area of the skirt 64' is large enough and smooth enough to be used as a support for a label.

Figure 6:
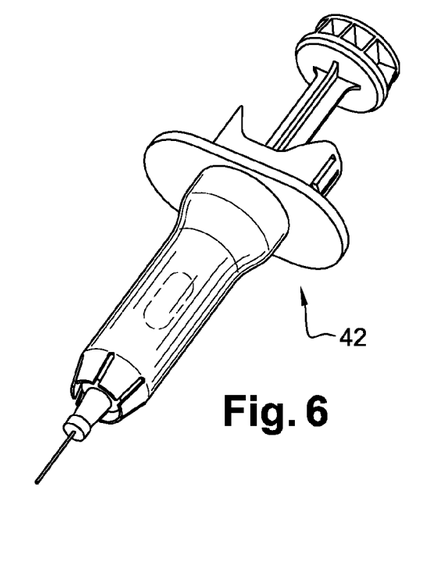
FIG. 6 is a perspective view of the assembly of a safety device and a syringe in a fifth embodiment.

In FIG. 6, the extender member 42 does not present an annular skirt 64.

Figure 7:
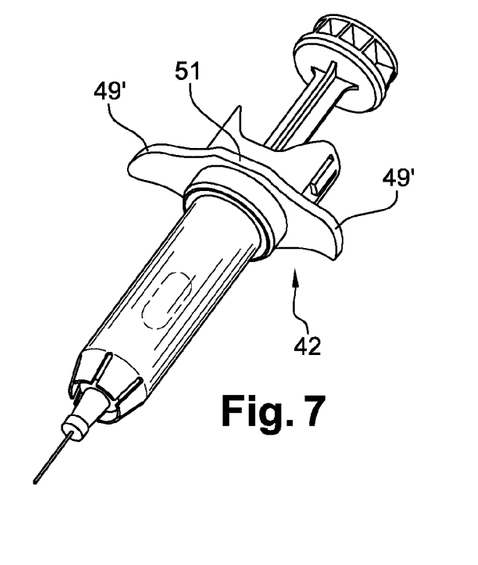
FIG. 7 is a perspective view of the assembly of a safety device and a syringe in a sixth embodiment.

In FIG. 7, the enlarged grip surface 46 presents two opposite radial ends 49', these ends being curved towards the distal end of the device 11.

It can be understood that the above-described extender member 42 enables the safety device to be manufactured with a size that is substantially standard, comprising the elements 40, 18, and 14, while still being capable of being adapted to a special utilization by adding the member 42. It is thus possible to customize the safety device 11. In particular, different extender members 42 may be provided from one device 11 to another, which members may be made with different colors, materials, or shapes.

It should be observed that the invention is not limited to the above-described embodiments. In particular, the characteristics of the various embodiments may naturally be combined with one another, or they may be used separately.

What is claimed is:

1. A safety device for an injection syringe, the safety device comprising:
   a syringe support;
   a protective sheath for protecting an injection needle carried by the injection syringe, the protective sheath being mounted to slide relative to said syringe support between an injection position in which the needle is uncovered, and a protection position in which the needle is covered, the protective sheath having an initial grip surface enabling the device to be gripped by a user, the initial grip surface being a projection that extends outward from the protective sheath in a radial plane substantially perpendicular to a longitudinal axis of the device; and
   a return spring for urging the protective sheath into the protection position;
   wherein the protective sheath also includes an extender member for extending the initial grip surface, being a separate piece from the protective sheath, attached to the protective sheath in such a manner as to present an enlarged grip surface, larger than the initial grip surface;
   wherein the extender member engages around an outer edge of the initial grip surface.

2. The device according to claim 1 wherein the extender member comprises an annular skirt projecting from the extender member.

3. The device according to claim 2, wherein the spring is in a compressed configuration when the protective sheath is in the injection position, and wherein the annular skirt masks the spring in the compressed configuration.

4. The device according to claim 2, wherein the protective sheath includes a mechanism for preventing the protective sheath from moving in the protection position, and the annular skirt covers said mechanism for preventing the protective sheath from moving.

5. The device according to claim 4, wherein the mechanism for preventing the protective sheath from moving in the protection position is a snap-fastener.

6. The device according to claim 4, wherein the mechanism for preventing the protective sheath from moving in the protection position is slots which engage with lugs on said syringe support.

7. The device according to claim 2, wherein the annular skirt extends in a longitudinal direction to a distal end of the device, so as to cover all of the needle of the syringe when the protective sheath is in the protection position.

8. The device according to claim 7, wherein the annular skirt comprises a main tubular portion and a distal end with a diameter that decreases relative to a diameter of the main tubular portion.

9. The device according to claim 1, wherein the extender member has two opposite radial ends, said ends being curved towards the longitudinal axis and a distal end of the device.

10. The device according to claim 1, wherein the enlarged grip surface includes anti-skid portions.

11. The device according to claim 1, wherein the extender member has two opposite radial ends that are rounded and connected together by two opposite flat sides.

12. The device according to claim 1, including a tamperproofing sleeve fastened to the device by a breakable connection.

13. The device according to claim 12, wherein the breakable connection is integrally molded with the extender member.

14. An assembly of the safety device according to claim 1 and the injection syringe comprising a pre-filled syringe.

15. A method of assembling the device according to claim 1, wherein a portion of the protective sheath is initially assembled with said syringe support, after which the extender member is fitted on said portion of the protective sheath.

16. The device according to claim 1, wherein the extender member surrounds the outer edge of the initial grip surface.

17. The device according to claim 1, wherein the extender member engages the outer edge of the initial grip surface via fastener lugs on the extender member.

18. The device according to claim 1, wherein the extender member includes a cavity which receives the initial grip surface and extends around the outer edge of the initial grip surface.

19. The device according to claim 1, wherein the initial grip surface comprises at least two diametrically opposite portions in a form of grip flanges.

20. The device according to claim 1, wherein the initial grip surface is in a form of a circular collar extending around the protective sheath and lying in the radial plane.

* * * * *